Aug. 19, 1947. A. KREBS Plant Pat. 752
ROSE PLANT
Filed Jan. 26, 1946
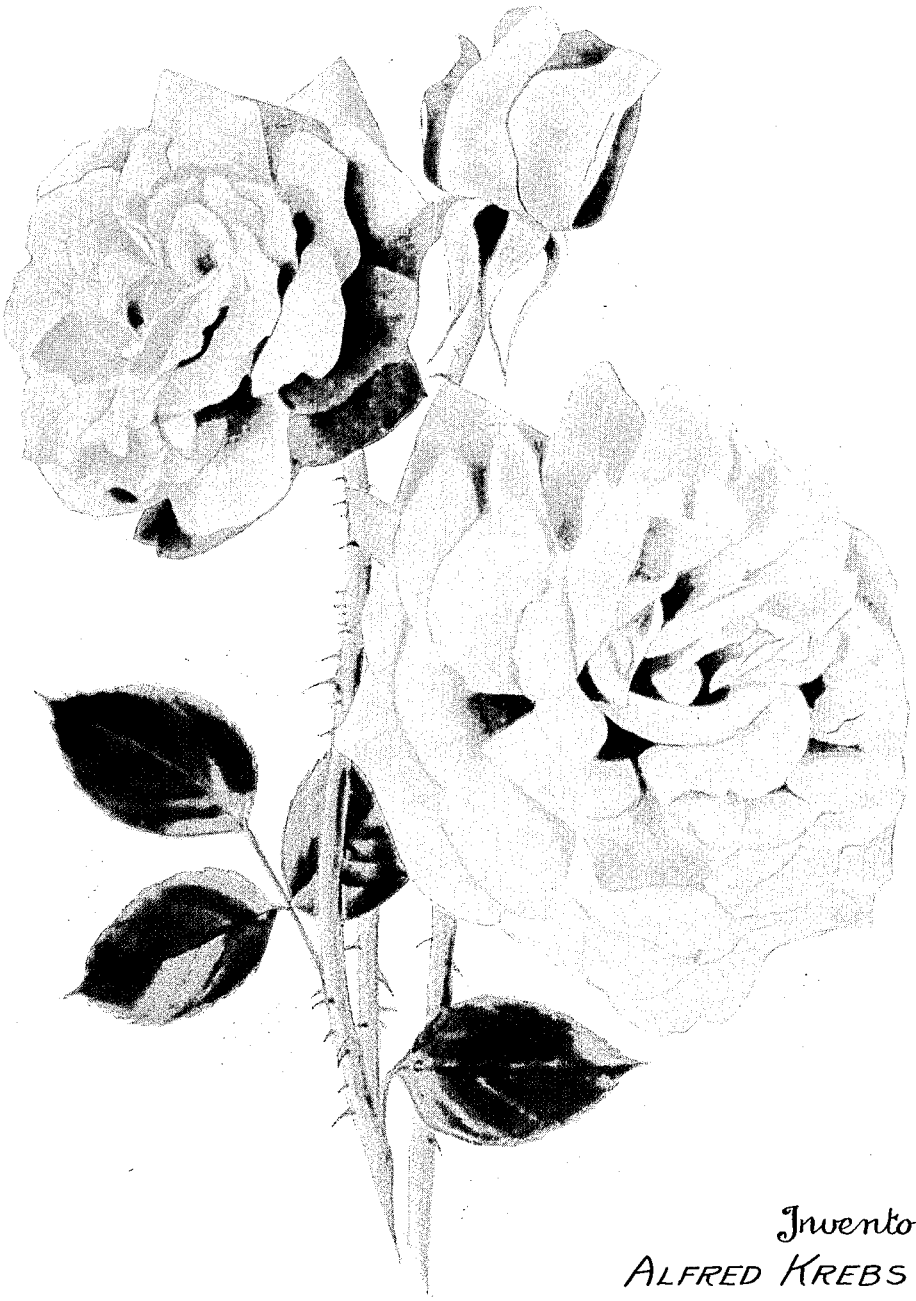
Inventor
ALFRED KREBS
By Lyon & Lyon
Attorneys Patented Aug. 19, 1947

Plant Pat. 752

UNITED STATES PATENT OFFICE

752

ROSE PLANT

Alfred Krebs, Montebello, Calif., assignor of one-half to Edward E. Marsh, Pasadena, Calif.

Application January 26, 1946, Serial No. 643,542

1 Claim. (Cl. 47—61)

This invention relates to a new and distinctive variety of rose which has as its parentage the E. G. Hill rose crossed with the Queen Alexandria rose.

The rose was produced through cross-pollenization of these rose varieties, and the cross-polenization having been carried out at Montebello, California.

The new and distinctive variety of rose embracing this invention is characterized by the following:

1. Color: Generally designated as red and specifically hereinafter described.

2. The shape and size of the bud and rose in full bloom, which are particularly illustrated in the accompanying drawings, the bud being of relatively short length, of average size, and rather tightly closed, and having long sepals which are folded back rather uniformly onto the stem. The buds are pointed, forming to a cup shape as the buds develop larger.

The rose in full bloom is of multiple petal rather closely set and when in full bloom is of irregular pattern.

3. The rose is particularly characterized in its intense fragrance, which is long-lasting.

4. The rose is further characterized in being a continuous bloomer and particularly resistant to mildew. The bush is well shaped and the leaves are semi-glossy.

5. The rose is further characterized by its color, which is bright red, at times blending into scarlet.

6. The bush is further characterized by very heavy thorns, which are irregularly positioned upon the stems carrying the roses.

As the rose and its foliage are illustrated in the accompanying print, it is illustrated in a semi-open bud, together with two opened flowers, and the leaf structure. The color of the bud is shaded between Geranium Lake, Chart 20/1, and Carmine Chart 21, of the color plates of the Royal Horticultural Society Color Chart issued by the British Color Council.

The fully opened flower is of a color shading from Turkey Red, Chart 721, to a Carmine, Chart 21, at the darkest parts, to a lighter color comparable to Geranium Lake, Chart 20/1.

In the lighter shades of the flower shown in its fully open position, that is, the rose on the right of the drawing, the color characteristics are of the Carmine, Chart 21/1 to Chart 21/2 of the color plates of the aforesaid Royal Horticultural Society.

The leaves have a color shading from Parsley Green of Chart 00962/3 to a Willow Green, Chart 000862, of the color plates of the aforestated Royal Horticultural Society. The leaf texture is semi-glossy and is barbed and is relatively wide compared with their length as distinguished from the long, narrow-leafed type of rose-bushes.

The rose of this invention is of the bush type as distinguished from a climber.

The rose of this invention is further characterized by its hardy growing characteristics, being a rose that develops extremely rapidly from the budded stock to a full blooming bush and differentiated from most rapidly growing rose bushes, is resistant to mold, mildew, and is pest-resistant.

I claim:

The variety of bush rose plant herein disclosed, characterized by its Geranium Lake to Carmine coloring, developing into a multiple-petaled, fully-opened rose, the coloring shading between Turkey Red, Carmine, and Geranium Lake, and characterized in its extremely rapid growth qualities, its intense fragrance, and its thorny stem structure, and further characterized in that it is resistant to mildew and pest infestation, and having as its parentage the E. G. Hill and Queen Alexandria bush roses.

ALFRED KREBS.